(12) United States Patent
Cole et al.

(10) Patent No.: US 7,369,242 B2
(45) Date of Patent: May 6, 2008

(54) CAVITY RING-DOWN SPECTROMETER FOR SEMICONDUCTOR PROCESSING

(75) Inventors: Barrett E. Cole, Bloomington, MN (US); Yuandong Gu, Plymouth, MN (US)

(73) Assignee: Honeywell International Inc., Morristown, NJ (US)

( * ) Notice: Subject to any disclaimer, the term of this patent is extended or adjusted under 35 U.S.C. 154(b) by 131 days.

(21) Appl. No.: 11/384,017

(22) Filed: Mar. 17, 2006

(65) Prior Publication Data

US 2007/0216903 A1 Sep. 20, 2007

(51) Int. Cl.
*G01N 21/00* (2006.01)

(52) U.S. Cl. .................. 356/436; 356/73; 356/519

(58) Field of Classification Search ........ 356/432–437, 356/73, 519, 454
See application file for complete search history.

(56) References Cited

U.S. PATENT DOCUMENTS

| | | | | |
|---|---|---|---|---|
| 5,528,040 | A | 6/1996 | Lehmann | 250/343 |
| 5,815,277 | A * | 9/1998 | Zare et al. | 356/437 |
| 5,835,231 | A | 11/1998 | Pipino | 356/440 |
| 5,912,740 | A | 6/1999 | Zare et al. | 356/437 |
| 5,955,139 | A * | 9/1999 | Iturralde | 427/9 |
| 5,959,297 | A | 9/1999 | Weinberg et al. | 250/288 |
| 6,075,252 | A | 6/2000 | Atkinson et al. | 250/559.4 |
| 6,084,682 | A | 7/2000 | Zare | |
| 6,400,744 | B1 | 6/2002 | Capasso et al. | 372/96 |
| 6,421,127 | B1 | 7/2002 | McAndrew et al. | 356/437 |
| 6,466,322 | B1 | 10/2002 | Paldus et al. | 356/437 |
| 6,541,271 | B1 | 4/2003 | McFarland et al. | 436/171 |
| 6,658,034 | B2 | 12/2003 | Garnache et al. | 372/45 |
| 6,727,492 | B1 | 4/2004 | Ye et al. | 250/227.18 |
| 6,768,548 | B2 | 7/2004 | Zare et al. | 356/432 |
| 6,795,190 | B1 | 9/2004 | Paul et al. | 356/437 |
| 6,816,636 | B2 | 11/2004 | Cole et al. | 385/10 |
| 6,839,140 | B1 | 1/2005 | O'Keefe et al. | 356/436 |
| 6,849,460 | B2 | 2/2005 | McFarland et al. | 436/171 |
| 6,865,198 | B2 * | 3/2005 | Taubman | 356/437 |
| 6,885,452 | B2 | 4/2005 | McAndrew | |
| 7,037,554 | B2 | 5/2006 | Tao et al. | 427/163.2 |
| 7,154,595 | B2 * | 12/2006 | Paldus et al. | 356/73 |
| 2003/0197860 | A1 | 10/2003 | Rice | |
| 2004/0180448 | A1 | 9/2004 | Lehmann et al. | 436/151 |
| 2005/0040337 | A1 | 2/2005 | Cox et al. | 250/343 |
| 2005/0052653 | A1 | 3/2005 | Fidric | |
| 2005/0206903 | A1 | 9/2005 | Tan et al. | 356/437 |
| 2006/0082778 | A1 | 4/2006 | Paldus et al. | 356/437 |
| 2006/0084180 | A1 | 4/2006 | Paldus et al. | 436/171 |
| 2006/0119851 | A1 * | 6/2006 | Bounaix | 356/437 |

OTHER PUBLICATIONS

PCT International Search Report and Written Opinion from corresponding PCT application, published Jul. 13, 2007.

* cited by examiner

*Primary Examiner*—Layla G. Lauchman
*Assistant Examiner*—Iyabo S Alli
(74) *Attorney, Agent, or Firm*—Kris T. Fredrick

(57) ABSTRACT

An apparatus is provided for measuring a gas within a semiconductor thin film process. The apparatus includes an optical resonator disposed within an environment of the thin-film process, a tunable laser that excites the optical resonator at a characteristic frequency of the gas and a detector that detects an energy within the resonator.

23 Claims, 1 Drawing Sheet

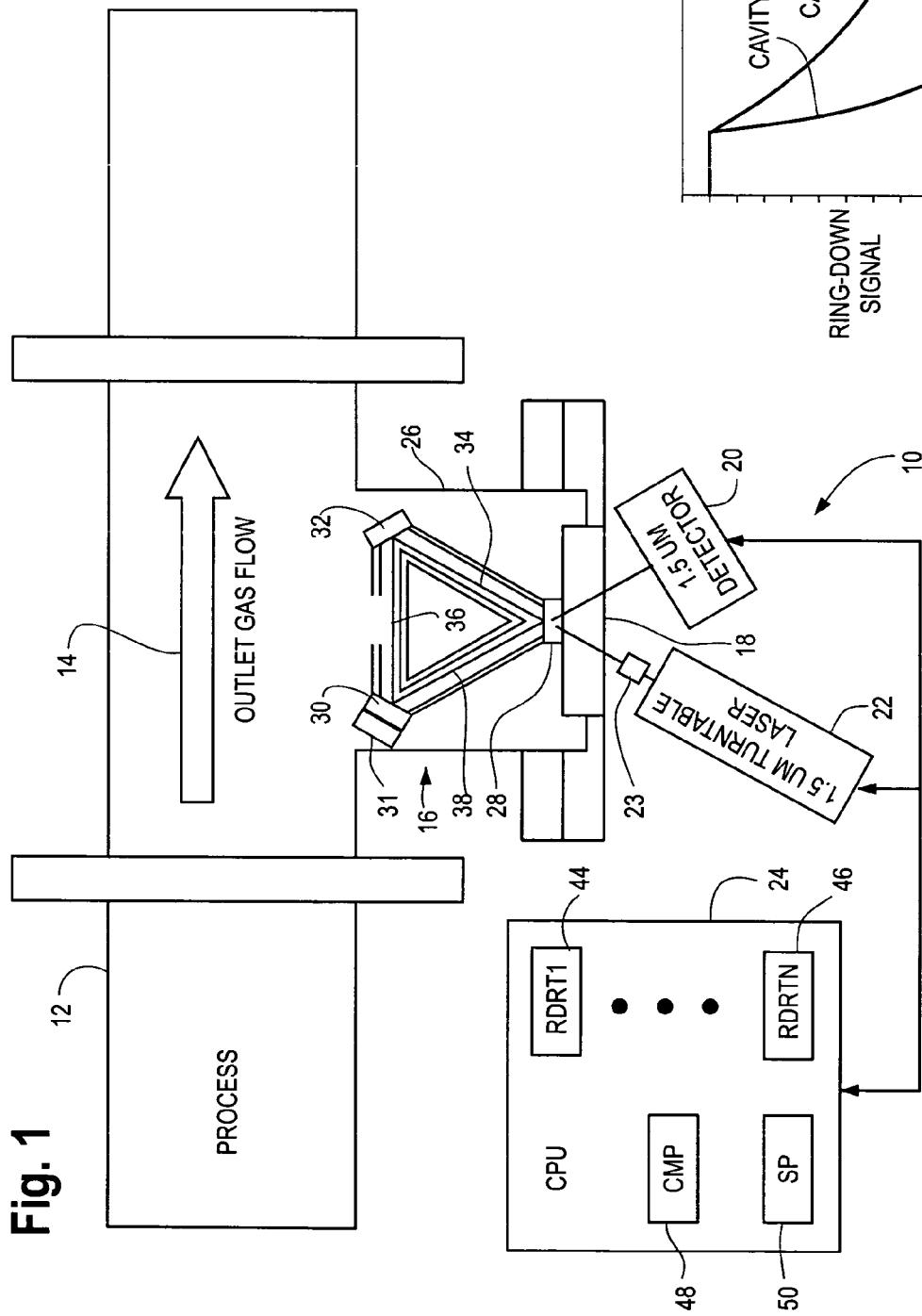
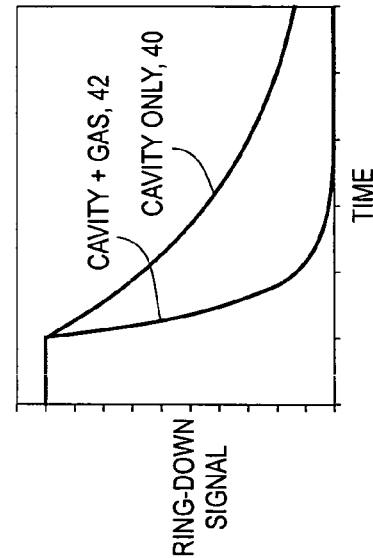
Fig. 2

CAVITY RING-DOWN SPECTROMETER FOR SEMICONDUCTOR PROCESSING

FIELD OF THE INVENTION

The field of the invention relates to semiconductor processing and more particularly to apparatus for detecting gas concentrations within a semiconductor processing environment.

BACKGROUND OF THE INVENTION

Control of an environment in the processing of semiconductors is very important. Typically, semiconductors are fabricated from wafers within a processing chamber. One or more diffusion steps may be followed (or preceded) by masking steps to define semiconductor fabrication sites on a wafer. Once fabrication sites have been defined, the process may be repeated any number of times depending upon the complexity of the fabricated device.

Once semiconductor devices have been created at the defined sites, a set of connections may be formed at the defined sites. Connections may be formed by any number of masking, deposition and etching steps.

At each step of the fabrication process, different reactive materials may be used. Usually the reactive materials are in the form of gases.

In order to provide a consistent semiconductor product, the diffusion, deposition and etching processes must be reliably controlled usually through the precise control of the reactive gases. Typically, this is accomplished by controlling the flow of the reactive materials into the processing chamber.

In semiconductor thin film processing, it is very important to know the precise gas composition within the processing chamber. Conventionally, this is accomplished primarily by flow controls, but flow control alone does not identify the proportions of reactant gas present within the processing chamber especially when there are other gases present, such as carrier gases or background gases. Accordingly, a need exits for a better method of measuring gas content, especially in a process environment involving a multitude of gases.

BRIEF DESCRIPTION OF THE DRAWINGS

FIG. 1 is a block diagram of a gas concentration measuring system in accordance with an illustrated embodiment of the invention; and FIG. 2 is a ring down profile of the resonator of FIG. 1 in the presence of a predetermined gas and under excitation of a characteristic frequency of the predetermined gas.

DETAILED DESCRIPTION OF THE INVENTION

An apparatus is provided for measuring a gas within a semiconductor thin film process. The apparatus includes an optical resonator disposed within an environment of the thin-film process, a tunable laser that excites the optical resonator at a characteristic frequency of the gas, a detector that detects an energy within the resonator and a processor that detects a concentration of the gas based upon a ring down rate of the detected energy.

Turning now to the drawing, FIG. 1 is a block diagram of a gas detection system 10, shown in a context of use generally in accordance with an illustrated embodiment of the invention. As shown in FIG. 1, the detection system 10 may be used to monitor gas concentrations within a semiconductor thin film process 12. While the system 10 is shown as being used to detect gas concentration in an outlet gas flow (stream) 14, it should be understood that the system 10 could just as well be used to detect an inlet gas flow into the process 12.

The detection system 10 may include an optical resonator 16, an optical detector 20, a tunable laser 22 and a central processing unit (CPU) 24. The tunable laser may be tunable over some appropriate optical wavelength range (e.g., 1-12 micrometers).

The optical resonator 16 may be placed directly in the outlet gas flow 14 or offset from the gas stream within a "T" connection 26 as shown in FIG. 1. As would be known to those of skill in the art, the input and output gas flows of the process 12 may include a number of very corrosive gases. Since the optical resonator 16 is located in the gas stream, the optical resonator 16 may be fabricated of materials that are resistant to those gases. With suitable protective provision, the tunable laser 22 and detector 20 may also be located within the gas stream 14 or may interact with the resonator 16 through an optically transparent window 18 that functions to isolate the process environment from the instrument environment.

The window 18 may be fabricated of an appropriate optical glass (e.g., quartz glass). Alternatively, the window 18 may be fabricated from sapphire.

The optical resonator 16 may consist of three mirrors 28, 30, 32 in the form of a triangle. The tunable laser 22 may be aligned coaxially with a first leg 34 of the triangle. Optical energy entering the resonator 16 through the first mirror 28 propagates along the first leg 34 of the resonator 16 and is reflected by a second mirror 32. Reflected energy from the second mirror 32 propagates along a second leg 36 to the third mirror 30 and is reflected along a third leg 38 to the first mirror 28. The sum total of the lengths of the legs 34, 36, 38 may be an integral multiple of the resonant frequency.

At the first mirror 28 most of the optical energy is reflected along the first leg 34 and recirculates around the triangle. However, at least some of the energy propagating along the third leg 38 passes through the first mirror 28 and impinges on the detector 20 coaxially aligned with the third leg 38.

In general, the gas detection system 10 functions in accordance with the principles of spectroscopy. As is known, each gas in the gas stream 14 absorbs optical energy at wavelengths that are characteristic for the gas. By tuning the tunable laser 22 to a characteristic frequency of a predetermined gas, the system 10 can measure the concentration of the predetermined gas independently of the presence or concentrations of other gases within the gas stream 14. As is known, the greater the concentration of the predetermined gas, the greater the absorption of the characteristic wavelength of optical energy.

In order to measure gas concentrations, the tunable laser 22 may be tuned to a characteristic wavelength of the gas. A simple mechanical servo 31 may be used to adjust the sum length of the three legs 34, 36, 38 to an integral multiple of the selected wavelength.

The tunable laser 22 may be pulsed at some predetermined rate (e.g., 50 pulses per second) to deliver optical pulses of an appropriate duration (e.g., a few nanoseconds) to the resonator 16. Pulsing may be accomplished through use of a shuttering device (e.g., an acousto-optic modulator).

The application of the pulses to the resonator 16 causes the optical energy to recirculate around the resonator 16 (i.e., the resonator 16 "rings"). The decay rate (i.e., the "ring down rate") of the optical energy within the resonator 16 depends upon the wavelength of the optical energy, the gas within the stream 14 and the optical losses of the resonator 16.

FIG. 2 is an example of an amplitude versus time graph that shows ring down rates of the resonator 16 in the case of a predetermined gas and the resonator 16 resonating at the characteristic wavelength of the predetermined gas. As shown, the resonator 16 would have a first characteristic curve 40 in a vacuum and a second characteristic curve 42 in the presence of some maximum concentration of the predetermined gas. Any concentration of the predetermined gas below the maximum concentration would have its characteristic curve somewhere between curves 40 and 42. The group of curves of FIG. 2 represents a ring down rate profile for the predetermined gas.

In order to determine a concentration of the predetermined gas in the gas stream 14, the group of curves and corresponding gas concentration value of FIG. 2 may be incorporated into a ring down rate look up table 44 in a memory of CPU 24. Within the table 44, each curve 40, 42 within the ring down rate profile may be saved as a locus of points or as an equation that characterizes the curve 40, 42.

In order to determine the concentration of the predetermined gas within the stream 14, the CPU 24 may cause the tunable laser 22 to tune to the characteristic wavelength of the predetermined gas and impose a sequence of optical pulses on the resonator 16. After each pulse, a sampling processor 50 may detect an amplitude of the resonating optical energy within the resonator 16 over a predetermined set of time intervals. The amplitude and time value at each sample point together define coordinates within a sample curve. The sampling processor 50 may transfer the coordinates of each sample curve to a curve matching processor 48.

Within the curve matching processor 48, the sample curve may be matched with at least one of the curves within the ring down profile of the predetermined gas. The curve matching processor 48 identifies the curve 40, 42 with the closest match and selects the gas concentration value associated with that curve as the determined gas concentration.

Similarly, the gas detection system 10 may analyze and measure the concentration of any number of different gases (a set of predetermined gases) that are simultaneously present within the stream 14. In this case, a ring down rate lookup table file 44, 46 may be provided for each gas to be measured. In addition to a ring down rate profile for each gas to be measured, the file 44, 46 may include a set of characteristic wavelengths along with an identifier of the gas.

To measure a gas concentration, the CPU 24 may sequentially select each gas of the set and measure a concentration as described above based upon a characteristic wavelength of the selected gas. Where the system 10 is used for process control, the measured values may be transferred to a process controller (not shown) as feedback control for the process.

In general, the system 10 may be used to monitor gas constituents of the stream 14 from the parts per million (ppm) to the parts per billion (ppb) range by measuring gas absorption via changes in the ring down time for unique gas absorption wavelengths and then converting this to concentration using known absorption cross sections. A one ppm atmospheric concentration measurement at one bar translates to a one milliTorr (mTorr) accuracy. Thus if processing 100 mTorr of total gases, the concentration of the known gas can be known to 0.1% accuracy. Not only is this technique good for inlet gas mixtures, but it can be used to measure the amount of 1) unreacted post-process gases or 2) other gases resulting from the reaction.

A specific embodiment of a gas measuring system has been described for the purpose of illustrating the manner in which the invention is made and used. It should be understood that the implementation of other variations and modifications of the invention and its various aspects will be apparent to one skilled in the art, and that the invention is not limited by the specific embodiments described. Therefore, it is contemplated to cover the present invention and any and all modifications, variations, or equivalents that fall within the true spirit and scope of the basic underlying principles disclosed and claimed herein.

The invention claimed is:

1. An apparatus for measuring a gas within a semiconductor thin film process, such apparatus comprising:
    a reactive gas stream of the thin-film process;
    an optical resonator disposed within the reactive gas stream of the thin-film process;
    a tunable laser that excites the optical resonator at a characteristic frequency of the gas; and
    a detector that detects an energy within the resonator.

2. The apparatus for measuring a gas as in claim 1 further comprising a processor that detects a concentration of the gas based upon a ring down rate of the detected energy.

3. The apparatus for measuring a gas as in claim 2 further comprising a shuttering device disposed between the tunable laser and optical resonator that periodically interrupts optical energy from the optical resonator.

4. The apparatus for measuring the gas as in claim 2 wherein the processor further comprises a curve matching processor that matches the ring down rate of the resonator with a curve of a ring down profile of the gas.

5. The apparatus for measuring the gas as in claim 2 wherein the processor further comprises a lookup table of ring-down rates for the predetermined gas.

6. The apparatus for measuring the gas as in claim 1 wherein the thin film process further comprises a thin film processing chamber.

7. The apparatus for measuring the gas as in claim 6 further comprising an optically transparent window in an exterior wall of the thin-film processing chamber.

8. The apparatus for measuring the gas as in claim 7 further comprising the laser disposed outside the thin-film processing chamber and exciting the resonator through the optically transparent window.

9. The apparatus for measuring the gas as in claim 7 further comprising the detector disposed outside the thin-film processing chamber and receiving an optical signal from the resonator through the optically transparent window.

10. The apparatus for measuring the gas as in claim 9 wherein the resonator further comprises three optical reflectors arranged to reflect a resonating optical signal along a triangular path.

11. The apparatus for measuring the gas as in claim 10 further comprising an optical reflector of the three optical reflectors disposed adjacent the optically transparent window.

12. The apparatus for measuring the gas as in claim 10 further comprising a servo that adjusts a distance between the three optical reflectors to an integral multiple of the characteristic frequency of the gas.

13. An apparatus for measuring a quantity of a predetermined gas within a semiconductor thin film processing chamber, such apparatus comprising:
    a thin film processing chamber;

a reactive gas stream flowing through the thin-film processing chamber;
an optical resonator disposed within the reactive gas stream;
a tunable laser that excites the optical resonator at an absorption wavelength of the predetermined gas;
a detector that detects a ring down rate of the resonator after excitation; and
a processor that determines the quantity of the gas within the thin film processing chamber based upon the detected ring down rate of the resonator.

14. The apparatus for measuring the gas as in claim 13 further comprising an optically transparent window in an exterior wall of the thin-film processing chamber.

15. The apparatus for measuring the gas as in claim 14 further comprising the laser disposed outside the thin-film processing chamber and exciting the resonator through the optically transparent window.

16. The apparatus for measuring the gas as in claim 14 further comprising the detector disposed outside the thin-film processing chamber and receiving an optical signal from the resonator through the optically transparent window.

17. The apparatus for measuring the gas as in claim 16 wherein the resonator further comprises three optical reflectors arranged to reflect a resonating optical signal along a triangular path.

18. The apparatus for measuring the gas as in claim 17 further comprising an optical reflector of the three optical reflectors disposed adjacent the optically transparent window.

19. The apparatus for measuring the gas as in claim 18 further comprising the laser coaxial aligned with a first leg of the triangular path through the optically transparent window and the one optical reflector adjacent the optically transparent window.

20. The apparatus for measuring the gas as in claim 18 further comprising the detector coaxial aligned with a second leg of the triangular path through the optically transparent window and the one optical reflector adjacent the optically transparent window.

21. The apparatus for measuring the gas as in claim 13 wherein the processor further comprises a lookup table of ring-down rates for the predetermined gas.

22. The apparatus for measuring the gas as in claim 13 wherein the processor further comprises a curve matching processor that matches the detected ring down rate of the resonator with a curve within a ring down profile of the predetermined gas.

23. An apparatus for measuring a gas within a semiconductor thin film processing chamber, such apparatus comprising:
an optically transparent window in an exterior wall of the thin-film processing chamber;
a reactive gas stream flowing through the thin-film processing chamber;
an optical resonator disposed within the reactive gas stream;
a tunable laser disposed outside the thin-film processing chamber that excites the optical resonator through the optically transparent window;
a detector disposed outside the thin-film processing chamber that detects a ring-down time; and
a lookup table that is used to determine the gas within the thin film processing chamber based upon the ring-down time of the resonator.

* * * * *